US009145995B2

(12) United States Patent
Gastauer et al.

(10) Patent No.: US 9,145,995 B2
(45) Date of Patent: Sep. 29, 2015

(54) ADAPTER FOR CONNECTING A RECEPTACLE CONNECTOR TO A COUPLING SOCKET OF A DIALYSIS MACHINE

(75) Inventors: Paul Gastauer, Hong Kong (CN); Philippe Laffay, Sainte Foy les Lyon (FR); Bruno Faye, Les Olmes (FR)

(73) Assignee: FRESENIUS MEDICAL CARE DEUTSCHLAND, Bad Homburg (DE)

( * ) Notice: Subject to any disclaimer, the term of this patent is extended or adjusted under 35 U.S.C. 154(b) by 279 days.

(21) Appl. No.: 13/257,443

(22) PCT Filed: Mar. 17, 2010

(86) PCT No.: PCT/EP2010/053435
§ 371 (c)(1),
(2), (4) Date: Nov. 29, 2011

(87) PCT Pub. No.: WO2010/106091
PCT Pub. Date: Sep. 23, 2010

(65) Prior Publication Data
US 2012/0068455 A1    Mar. 22, 2012

(30) Foreign Application Priority Data
Mar. 20, 2009  (FR) .................................. 09 51791

(51) Int. Cl.
*F16L 7/00*          (2006.01)
*F16L 37/56*         (2006.01)
(Continued)

(52) U.S. Cl.
CPC .............. *F16L 37/56* (2013.01); *A61M 1/1656* (2013.01); *A61M 39/105* (2013.01); *A61M 39/1011* (2013.01); *A61M 2039/1027* (2013.01); *A61M 2039/1077* (2013.01)

(58) Field of Classification Search
USPC .................. 285/122.1, 123.1, 123.12, 123.15
See application file for complete search history.

(56) References Cited

U.S. PATENT DOCUMENTS 5,203,384 A * 4/1993 Hansen ........................... 141/59
5,509,148 A * 4/1996 Steele et al. .................. 4/255.01
(Continued)

FOREIGN PATENT DOCUMENTS

DE    4303372 A1    8/1994
EP    1344550 A1    9/2003
(Continued)

OTHER PUBLICATIONS

International Search Report of PCT/EP2010/053435, mailing date May 3, 2010.

*Primary Examiner* — Daniel P Stodola
*Assistant Examiner* — Gwendolyn Driggers

(57) ABSTRACT

Adapter (3) for connecting a receptacle connector to a connection socket of a dialysis machine, each provided with two fluid lines, whose ends are concentric on the connector and non-concentric and distant from each other on the socket. The adapter (3) has concentric first (301) and second (302) adapter ribs, the first forming a circular chamber open towards the outside, in the bottom of which a first orifice is produced, while the second forms an annular chamber open towards the outside, in the bottom of which a second orifice is produced. The adapter also has first and second connection channels (306, 307) isolated from each other, in which the first and second orifices coming from the first and second annular chambers open out. Each channel (306, 307) includes a connecting piece (308, 309) consisting of a circular tube, for introduction into the reception elements of the coupling socket (2).

18 Claims, 3 Drawing Sheets

Figure 1:
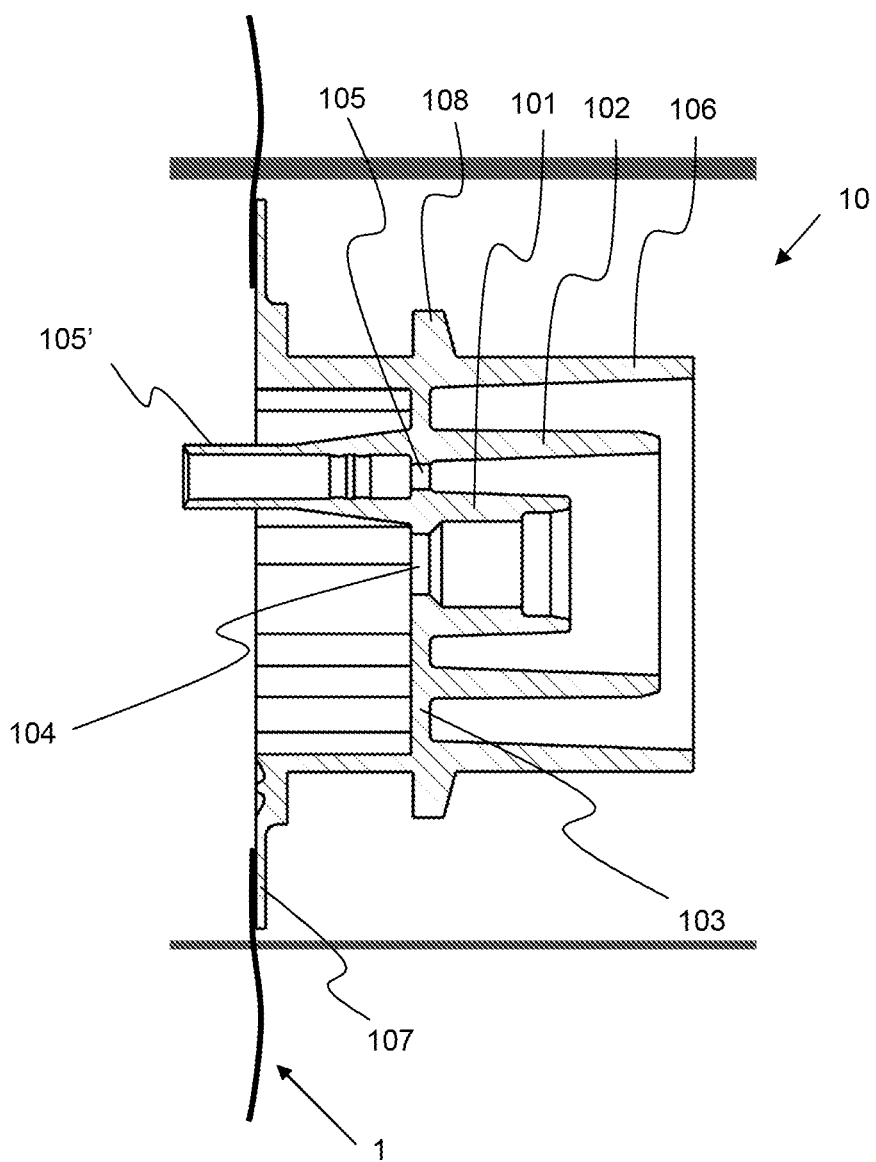

(51) Int. Cl.
*A61M 1/16* (2006.01)
*A61M 39/10* (2006.01)

(56) References Cited

U.S. PATENT DOCUMENTS 5,908,055 A * 6/1999 Baumann et al. ............... 141/59
6,508,272 B1 * 1/2003 Parsons et al. ................ 137/595
7,223,262 B2 * 5/2007 Brehm et al. .................. 604/415
7,572,981 B2 * 8/2009 Koizumi et al. ............... 174/111
2003/0168120 A1 9/2003 Brehm et al.
2004/0194918 A1 10/2004 Kato et al.

FOREIGN PATENT DOCUMENTS

FR 2766797 A1 2/1999
GB 1360732 A 7/1974
WO 2007/082548 A1 7/2007

* cited by examiner

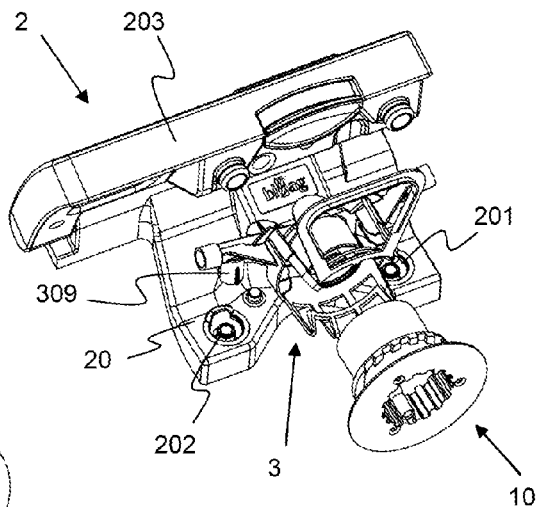
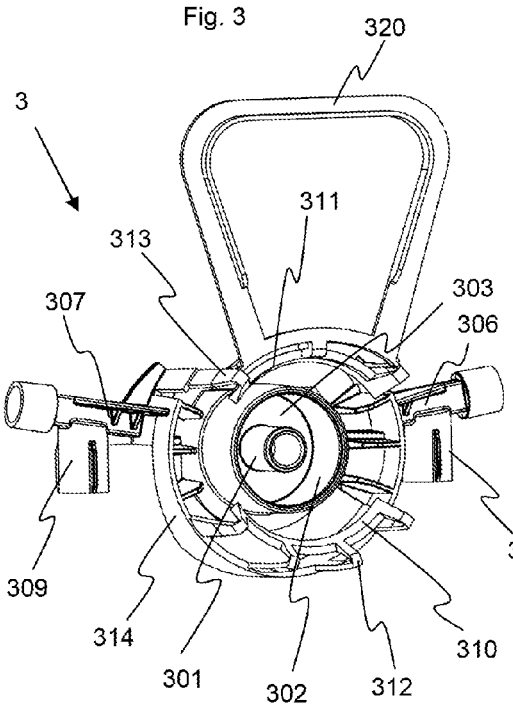
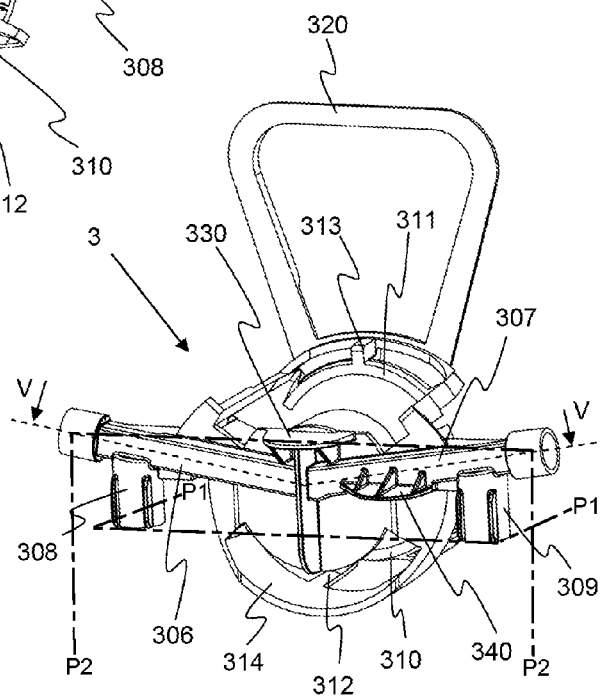

ADAPTER FOR CONNECTING A RECEPTACLE CONNECTOR TO A COUPLING SOCKET OF A DIALYSIS MACHINE

The invention concerns an adapter for connecting a receptacle connector to a connection socket of a dialysis machine, the connector being provided with two fluid lines connecting the inside and outside of the receptacle, the ends of which, open towards the outside, are concentric, the connection sockets of the dialysis machine being provided with two fluid lines, the ends of which, open towards the outside, are non-concentric and distant from each other.

Many dialysis machines are equipped with means for themselves manufacturing the dialysis solutions from water and a concentrate. This concentrate may be in the form of a concentrated solution or a powdery or granular solid product. These are in general salts. For producing the solution, the machine must introduce water into the pouch and the solution thus produced must be sucked in by the machine and then diluted.

The cartridges or pouches are therefore provided with a connector, the shape of which is complementary to that of the connection socket on the dialysis machine. Unfortunately, each type of dialysis machine has its own connection socket, even in a range of machines from the same company. As a result, the cartridges or pouches containing the same product must be offered in various forms, one and the same pouch not necessarily being compatible with two different machines.

The document WO 2007/082548 thus proposes a cartridge with two sets of connectors, one for a machine of the Gambro brand and the other for a machine of the Fresenius brand. Consequently the same cartridge can be used on two different machines. However, each cartridge is used only once on one or the other of the machines, so that only one of the sets of connectors will actually be used. This therefore involves significant additional costs.

Among the machines from the Fresenius company, it is known that some machines work with connectors with concentric fluid lines and other machines have separate fluid lines. In the case of concentric connectors, the operating principle of which is presented in the documents DE 43 03 372 A1 and FR 2 766 797 A1, the fluid lines, used for bringing the water and then sucking in the solution, have their ends directed towards the outside of the concentric flask. This results in a first fluid line opening into a first circular chamber delimited by a first rib and a second fluid line opening into an annular chamber situated around the first chamber. This second chamber is defined by the first rib and by a second rib situated around it concentrically. These connectors are usually placed on one of the vertical faces of the cartridge or pouch.

The connection socket of the dialysis machine has a corresponding shape for achieving, after assembly, the continuity of the fluid lines of the receptacle and of the machine.

In the case of separate fluid lines, the principle of which is presented in the document EP 1 344 550 A1, the connector is provided with two separate fluid lines, the external ends of which terminate in two connecting pieces that are introduced into two corresponding orifices on the dialysis machine. The connecting pieces are placed at a distance from each other and provide the junction between the fluid lines of the connector and those of the machine. The two outlets are no longer concentric but parallel.

The objective of the invention is to develop a means for allowing the use of cartridges or pouches provided with a concentric connector on a dialysis machine having a connection socket with separate fluid lines.

This objective is achieved according to the invention in that the adapter is provided with first and second concentric adapter ribs, the first forming a circular chamber open towards the outside, in the bottom of which a first orifice is provided, while the second, placed around the first, forms an annular chamber open towards the outside, in the bottom of which a second orifice is provided, the adapter also being provided with a first connection channel in which the first orifice coming from the first circular chamber opens out and a second connection channel isolated from the first, in which the second orifice coming from the second annular chamber opens out, each channel comprising a connecting piece, the said connecting pieces being sized and disposed so that they can be introduced into the reception elements of the connection socket of the dialysis machine. By virtue of this adapter, it is possible to convert an output of concentric fluid lines into an output of parallel fluid lines.

In order to facilitate the fitting of the adapter on the parallel connection socket, it is preferable for the axes of the connecting pieces to be parallel and for the ends of the connecting pieces to be disposed in a same plane perpendicular to the axes of the connecting pieces. Thus, it will be very simple to plug the two connecting pieces downwards into the corresponding receiving orifices in the connection socket on the machine.

When the adapter is intended for a pouch or receptacle having a connector placed on one of its vertical faces, it is preferable for the axes of the connecting pieces to be perpendicular to the axis of the concentric ribs. Thus, in the mounted position, the pouch keeps its vertical position.

According to the invention, the first adapter rib and the second adapter rib are sized so that, when the adapter is mounted on a concentric connector, they fit on or in corresponding first and second ribs of the connector so that the two concentric chambers are isolated from each other and vis-à-vis the outside.

So that the adapter does not become detached from the connector, hooking means are provided in order to hold the adapter on the connector in the position of use. These hooking means preferably consist of at least one arch mounted on hooks.

In a particular embodiment of the invention, the channels are not aligned and form an obtuse angle between them.

In order to make it possible to lift the receptacle when it is fitted with the adapter, it is preferable to provide the latter with a handle.

It is preferable to provide the adapter with retaining means, in particular a support plate, intended to cooperate with complementary means on the dialysis machine, in particular a cover, to prevent the adapter from pivoting under the effect of weight when it is mounted in the machine.

In a favoured embodiment of the invention, the adapter is provided with a detection plate intended to cooperate with complementary detection means on the dialysis machine.

The invention also concerns a set constituted by an adapter according to one of the previous claims and a receptacle equipped with a connector to connect the receptacle with a connection socket of a dialysis machine, the connector being equipped with two fluid lines connecting the inside and the outside of the receptacle, the extremities of which, open to the outside, are concentric. The receptacle can be, for example, a pouch or a cartridge.

Figure 5:
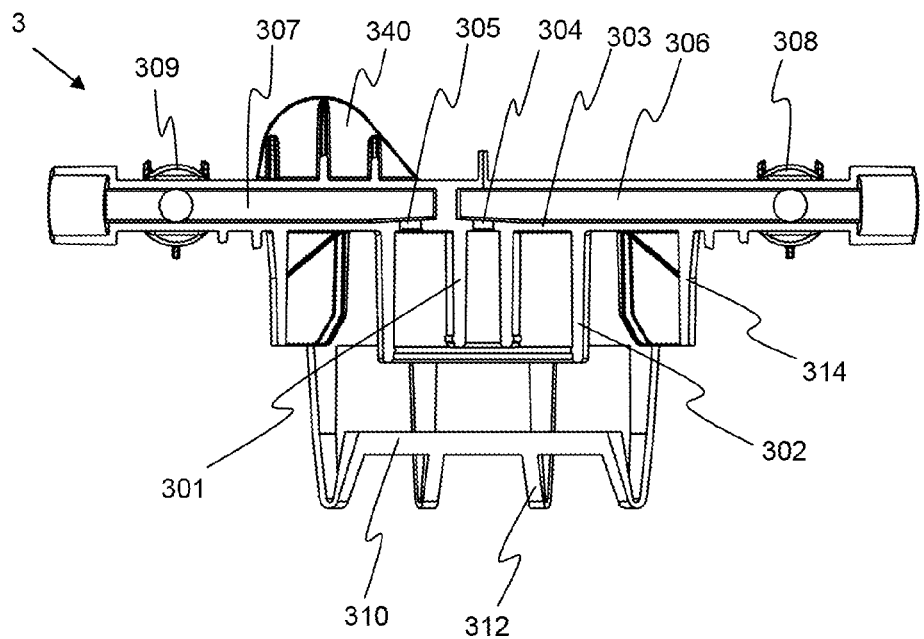
Figure 6:
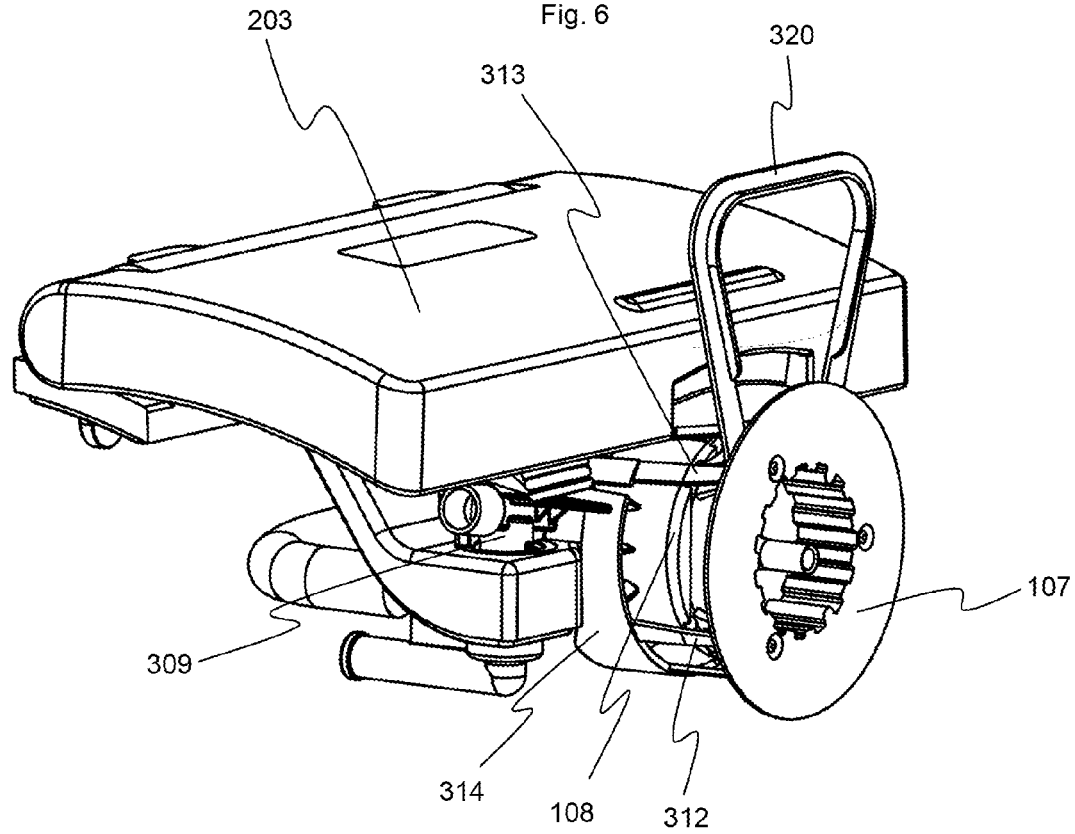

The invention is described in more detail with the help of the following figures, which show:

FIG. 1: a cross-sectional view of a circular connector;

FIG. 2: a perspective view of a connection socket of a dialysis machine with parallel fluid lines;

FIG. 3: a perspective front view of an adapter according to the invention;

FIG. 4: a perspective back view of an adapter according to FIG. 3;

FIG. 5: a cross-sectional view through the connection channels of the adapter of FIG. 3 along the line V-V in FIG. 4;

FIG. 6: a perspective view of an adapter according to FIG. 3, mounted on a circular connector of FIG. 1 and placed in a dialysis machine of FIG. 2.

An objective of the adapter of the invention is to allow the use of a receptacle provided with a concentric connector on a dialysis apparatus intended to receive receptacles provided with connectors with separate and distant fluid line entries.

A concentric connector (10) consists essentially of two concentric connector ribs (101, 102) placed perpendicularly on a circular base (103). Orifices (104, 105) are formed in the circular base (103). These orifices can be extended inside the receptacle by pipes immersed in the receptacle (1), such as the tube (105'). The first orifice (104) is placed inside the first rib (101), the central rib, and the second orifice (105) is placed in the space lying between the first (101) and second (102) ribs. The circular connector is therefore provided with two fluid lines each defined by at least one orifice (104, 105) and a channel formed, for the first fluid line, by the internal space of the first rib (101), and for the second fluid line, by the annular channel defined by the space situated between the first (101) and second (102) ribs. On the outside, the ends of the two fluid lines to be connected are therefore concentric.

In general, the concentric connector also comprises a third rib (106), concentric with the other two (101, 102) and placed outside these, which is extended beyond the base (103) and ends in a collar (107) to which the receptacle (1) is welded. To allow secure fixing of the connector on the dialysis apparatus, a second collar (108) is also provided, on which hooks fixed to the dialysis machine will be attached. This second collar (108) is placed on the outside of the connector with respect to the collar (107) for welding the receptacle.

The connection socket (20) of a dialysis machine with two parallel separate fluid lines comprises two vertical orifices (201, 202) in which fluid lines leading to the inside of the machine, which are not shown, emerge. These vertical orifices (201, 202) are parallel and are situated in a same horizontal plane P1 at a predefined distance on the ends of a U. For the dialysis machine 5008 from Fresenius, this distance is in the order of 70 mm. These orifices serve, on the one hand, as a coupling for the fluid lines of the connector of the receptacle and those of the machine, and on the other hand, as a support for the receptacle connector. A cover (203) is folded over the connector to hold it in place.

The adapter of the invention is therefore designed to separate the concentric fluid lines of the connector and to obtain two separate fluid lines each terminating in a connecting piece, the dimensions and locations of which are compatible with the connection socket of the dialysis apparatus.

The adapter (3) of the invention consists of a base plate (303) from which two concentric adapter ribs start perpendicularly in a same plane P2: the central rib (301), referred to as the first rib, and the external rib (302), referred to as the second rib. There is therefore a first, circular chamber delimited, on the one hand, by the first rib (301), and on the other hand, by the base plate (303), and a second, annular chamber delimited, on the one hand, by the first (301) and second (302) ribs, and on the other hand, by the base plate (303). These two chambers are open towards the outside, that is to say, on the side by means of which the connector (10) is introduced.

The base place (303) is provided with two orifices (304, 305) and two channels (306, 307) that start substantially from the centre of the base plate and diverge from each other. The channels are preferably placed on the face of the base plate (303) opposite to the ribs (301, 301).

The first orifice (304) connects the first chamber, that is to say, the space inside the first adapter rib (301), and the first channel (306), while the second orifice (305) connects the second channel (307) and the second chamber, and thus, the space situated between the first (301) and second (302) adapter ribs. The two channels do not communicate. At a distance from the base plate (303), each channel (306, 307) is provided with a connecting piece (308, 309), the dimensions of which are compatible with those of a dialysis machine with separate fluid lines. In the example presented, the connecting pieces (308, 309) are perpendicular to the ribs (301, 302). This therefore makes it possible to connect to the machine a receptacle whose connector (1) is situated on one of its vertical faces.

The dimensions and positions of these adapter ribs (301, 302) with respect to the base plate (303) are chosen so that they correspond to the connector ribs (101, 102) of the connector (10) of the receptacle. For example, the first adapter rib (301) is sized so as to enter the space defined by the first connector rib (101), forming a fluidtight connection. The second adapter rib (302) comes to surround the second connector rib (102), forming a fluidtight connection. In other words, the first chamber and the second chamber, initially open towards the outside, are kept closed by the connector, and the fluid lines of the connector defined by the first orifice and first connector rib (104, 101) and second orifice and second connector rib (105, 102), respectively, are extended by fluid lines of the adapter defined by the first adapter rib, first orifice of the base plate, first channel, and first connecting piece (301, 304, 306, 308) and second adapter rib, second orifice of the base plate, second channel, and second connecting piece (302, 305, 307, 309), respectively.

In order to lock the adapter (3) on the connector (1), a hooking device (310, 311) is provided, consisting for example of two arches (310, 311) connected by several hooks (312, 313) to the base plate (303) via a third concentric rib (314). When the adapter (3) is mounted on a concentric connector (1), these hooking means (310, 311) come into engagement behind the collar (108) of the connector. By virtue of the inclination of the folded ends of the hooks (312, 313), it is easy to fit an adapter on the connector, as the hooks move away when their folded ends come to slide against the peripheral edge of the collar (108). However, once the arches (310, 311) are placed behind this collar (108), it is no longer possible to bring the adapter out inadvertently without breaking the hooks (312, 313) or the arches (310, 311).

In order to lock the adapter in the dialysis machine, the latter is provided with a cover (203) that comes to bear on a support plate (330) situated on the base plate (303), above the two channels (306, 307), perpendicular to the base plate (303) and parallel to the axis of the ribs (301, 302). Thus the flask, in abutment through its connecting pieces (308, 309) fitted in the corresponding receivers (201, 202) of the machine is prevented from tilting backwards by virtue of this locking of the support plate (330) by the cover (203).

To make it possible to lift the receptacle provided with an adapter according to the invention, provision is made for equipping the latter with a handle (320).

To allow the detection of the presence of the receptacle provided with the adapter, provision is made for equipping the latter (3) with a detection plate (330). When the receptacle provided with the adapter is fitted, the machine will be able to detect its present by virtue of a suitably placed detector.

It is preferable for the channels (306, 307) not to be aligned, but to form an obtuse angle with each other. In the example presented in the figures, this angle is around 162°. In other words, the channels ascend while diverging from the centre of the adapter, forming an angle of approximately 9° with respect to the horizontal.

For manufacturing the adapter, all materials suited to injection moulding and allowed by the pharmacopoeia can be used. Polyethylene, polypropylene, polysulfone, polyacetal, and polyoxymethylene (POM) are cited by way of example.

By virtue of the adapter according to the invention, it is possible to use cartridges or pouches provided with a concentric connector on a dialysis machine having a connection socket with separate fluid lines. This makes it possible to reduce the stock of receptacles, by limiting it to receptacles provided with concentric connectors.

The adapter of the invention can be supplied separately or in a set along with a receptacle containing the product to be dissolved, such as, for example, a pouch or a cartridge. In this case, it is preferable not to pre-mount it on the connector of the receptacle, so that the final user has a choice of mounting it or not, depending on the dialysis machine used.

LIST OF REFERENCES

1 Receptacle
10 Connector
101 First connector rib
102 Second connector rib
103 Base
104 First orifice
105 Second orifice
105' Tube extending the second orifice
106 Third connector rib
107 Receptacle fixing collar
108 Adapter fixing collar
2 Dialysis machine
201 First connection socket reception orifice
202 Second connection socket reception orifice
203 Cover
3 Adapter
301 First adapter rib
302 Second adapter rib
303 Base plate
304 First orifice
305 Second orifice
306 First channel
307 Second channel
308 First connecting piece
309 Second connecting piece
310 First hooking arch
311 Second hooking arch
312 First set of hooks
313 Second set of hooks
314 Third adapter rib
320 Handle
330 Support plate
340 Detection plate

The invention claimed is:

1. Dialysis set comprising (1) a receptacle having a connector, and (2) an adapter for connecting the connector of the receptacle to a connection socket of a dialysis machine provided with two connection socket fluid lines, ends of the connection socket fluid lines being open towards an outside of the connection socket and non-concentric and distant from each other,
    wherein the connector of the receptacle is provided with first and second connector fluid lines connecting an inside and an outside of the receptacle, ends of the connector fluid lines being open towards the outside of the receptacle and concentric,
    wherein the adapter comprises:
    concentric first and second adapter ribs, the first adapter rib forming a first chamber which is a circular chamber open towards an outside of the adapter, a first orifice being provided in a bottom of the first chamber, while the second adapter rib, placed around the first adapter rib, forms a second chamber which is an annular chamber open towards the outside of the adapter, a second orifice being provided in a bottom of the second chamber, the first and second chambers being concentric around a central axis of the first and second adapter ribs, wherein, in a position of use of the adapter, the first and second ribs are fittingly mounted on the connector of the receptacle so that the first chamber is in fluid communication with the first connector fluid line of the receptacle, the second chamber is in fluid communication with the second connector fluid line of the receptacle, and the first and second chambers are isolated from each other and from the outside of the adapter,
    a first connection channel in which the first orifice coming from the first chamber opens, and a second connection channel, isolated from the first connection channel, in which the second orifice coming from the second chamber opens, wherein the first and second connection channels are oriented substantially in a same plane substantially perpendicular to the central axis of the first and second adapter ribs,
    each of the first and second connection channels being extended by a respective connecting piece consisting of a circular tube, said connecting pieces being sized and disposed so that they are capable of being introduced into reception elements of the connection socket of the dialysis machine,
    a base plate oriented substantially perpendicular to the central axis of the first and second adapter ribs, the first and second adapter ribs extending from a face of the base plate, the first orifice and the second orifice being provided in the base plate; and
    at least one arch mounted on hooks which holds the adapter on the connector in the position of use of the adapter.

2. The dialysis set according to claim 1, wherein axes of the connecting pieces are parallel to each other and ends of the connecting pieces are disposed in a same plane as each other, said plane being perpendicular to the axes of the connecting pieces.

3. The dialysis set according to claim 2, wherein the first adapter rib and the second adapter rib are sized so that the first and second adapter ribs are capable of coming to fit on or in corresponding first and second ribs of the connector so that the first and second chambers are capable of being isolated from each other and from the outside of the adapter in a state of the adapter mounted on the connector.

4. The dialysis set according to claim 2, wherein the axes of the connecting pieces are perpendicular to the central axis of the first and second adapter ribs.

5. The dialysis set according to claim 4, wherein the first adapter rib and the second adapter rib are sized so that the first and second adapter ribs are capable of coming to fit on or in corresponding first and second ribs of the connector so that the first and second chambers are capable of being isolated from each other and from the outside of the adapter in a state of the adapter mounted on the connector.

6. The dialysis set according to claim 1, wherein the first adapter rib and the second adapter rib are sized so that the first and second adapter ribs are capable of coming to fit on or in corresponding first and second ribs of the connector so that the first and second chambers are capable of being isolated from each other and from the outside of the adapter in a state of the adapter mounted on the connector.

7. The dialysis set according to claim 1, wherein the first and second connection channels are not aligned with each other and form an obtuse angle between themselves.

8. The dialysis set according to claim 7, wherein the first adapter rib and the second adapter rib are sized so that the first and second adapter ribs are capable of coming to fit on or in corresponding first and second ribs of the connector so that the first and second chambers are capable of being isolated from each other and from the outside of the adapter in a state of the adapter mounted on the connector.

9. The dialysis set according to claim 7, wherein axes of the connecting pieces are parallel to each other and ends of the connecting pieces are disposed in a same plane as each other, said plane being perpendicular to the axes of the connecting pieces.

10. The dialysis set according to claim 9, wherein the first adapter rib and the second adapter rib are sized so that the first and second adapter ribs are capable of coming to fit on or in corresponding first and second ribs of the connector so that the first and second chambers are capable of being isolated from each other and from the outside of the adapter in a state of the adapter mounted on the connector.

11. The dialysis set according to claim 9, wherein the axes of the connecting pieces are perpendicular to the central axis of the first and second adapter ribs.

12. The dialysis set according to claim 11, wherein the first adapter rib and the second adapter rib are sized so that the first and second adapter ribs are capable of coming to fit on or in corresponding first and second ribs of the connector so that the first and second chambers are capable of being isolated from each other and from the outside of the adapter in a state of the adapter mounted on the connector.

13. The dialysis set according to claim 1, wherein the adapter comprises a handle.

14. The dialysis set according to claim 1, wherein the adapter comprises holding means for holding the adapter on the dialysis machine for preventing the adapter from pivoting under an effect of weight when the adapter is mounted on the dialysis machine.

15. The dialysis set according to claim 14, wherein the holding means comprises a support plate intended to cooperate with a complementary cover on the dialysis machine.

16. The dialysis set according to claim 1, comprising a detection plate, wherein the detection plate is intended to cooperate with a detector on the dialysis machine.

17. The dialysis set according to claim 1, wherein the first and second connection channels are disposed on a second face of the base plate opposed to the face from which the first and second adapter ribs extend.

18. The dialysis set according to claim 1, wherein the adapter is fittingly mounted on the connector of the receptacle.

* * * * *